(12) United States Patent
Lien et al.

(10) Patent No.: US 11,335,450 B2
(45) Date of Patent: May 17, 2022

(54) DEHYDRATION AMOUNT PREDICTION METHOD FOR HEMODIALYSIS AND ELECTRONIC DEVICE USING THE SAME

(71) Applicant: Wistron Corporation, New Taipei (TW)

(72) Inventors: Yu-Hui Lien, New Taipei (TW); Chih-Yi Chien, New Taipei (TW)

(73) Assignee: Wistron Corporation, New Taipei (TW)

( * ) Notice: Subject to any disclaimer, the term of this patent is extended or adjusted under 35 U.S.C. 154(b) by 196 days.

(21) Appl. No.: 16/576,790

(22) Filed: Sep. 20, 2019

(65) Prior Publication Data

US 2020/0411162 A1    Dec. 31, 2020

(30) Foreign Application Priority Data

Jun. 25, 2019    (TW) .................................. 108122191

(51) Int. Cl.
G16H 20/40         (2018.01)
G16H 50/20         (2018.01)
G16H 50/50         (2018.01)

(52) U.S. Cl.
CPC .............. *G16H 20/40* (2018.01); *G16H 50/20* (2018.01); *G16H 50/50* (2018.01)

(58) Field of Classification Search
CPC ........ G16H 20/40; G16H 10/60; G16H 50/70; G16H 10/40; G16H 50/30
See application file for complete search history.

(56) References Cited

U.S. PATENT DOCUMENTS

2013/0325356 A1*  12/2013  Elashoff ............... G01N 33/487
                                                                702/19
2019/0318818 A1*  10/2019  Chaudhuri ............. G16H 20/40

FOREIGN PATENT DOCUMENTS

CN        106529162        3/2017
CN        109411061        3/2019
WO   WO-2015073910 A1 *  5/2015  ........... A61B 5/7267

OTHER PUBLICATIONS

Ronco, Claudio, et al. "Baseline hydration status in incident peritoneal dialysis patients: the initiative of patient outcomes in dialysis (IPOD-PD study)." Nephrology Dialysis Transplantation 30.5 (2015): 849-858. (Year: 2015).*
"Office Action of Taiwan Counterpart Application", dated Apr. 9, 2020, p. 1-p. 17.

\* cited by examiner

*Primary Examiner* — Elaine Gort
*Assistant Examiner* — Constantine B Siozopoulos
(74) *Attorney, Agent, or Firm* — JCIPRNET

(57) ABSTRACT

A dehydration amount prediction method for hemodialysis and an electronic device using the same are provided, and the method includes the following steps. Physiological data and hemodialysis treatment data of a first patient are obtained. The first patient is determined to belong to one of groups, wherein the groups are respectively associated with a plurality of prediction models. A target prediction model corresponding to the one of the groups is selected from the prediction models. The physiological data and the hemodialysis treatment data are provided to the target prediction model to generate a recommended dehydration amount by the target prediction model.

16 Claims, 4 Drawing Sheets

| group | blood pressure variation trend | classification rule |
|---|---|---|
| group1-4 |  | blood pressure variation trend factor is less than Q1 |
| group2-4 |  | blood pressure variation trend factor is greater than Q1 but less than Q2 |
| group3-4 |  | blood pressure variation trend factor is greater than Q2 but less than Q3 |
| group4-4 |  | blood pressure variation trend factor is greater than Q3 |

DEHYDRATION AMOUNT PREDICTION METHOD FOR HEMODIALYSIS AND ELECTRONIC DEVICE USING THE SAME

CROSS-REFERENCE TO RELATED APPLICATION

This application claims the priority benefit of Taiwan application serial no. 108122191, filed on Jun. 25, 2019. The entirety of the above-mentioned patent application is hereby incorporated by reference herein and made a part of this specification.

BACKGROUND

1. Technical Field

The disclosure relates to a prediction method based on machine learning, and particularly to a dehydration amount prediction method for hemodialysis and an electronic device using the same.

2. Description of Related Art

Hemodialysis (also known as kidney dialysis) is one of common medical treatments. In the process of hemodialysis, blood is drained to a dialysis machine (also known as kidney dialysis machine) and then returned into the body. Specifically, blood is drained out of the body first, then urine toxins and water are removed by diffusion and ultrafiltration of a semi-permeable membrane, and finally blood is led back into the body. Generally speaking, after medical personnel finish setting various parameters of the dialysis machine, the course of hemodialysis can be started on a patient with the dialysis machine.

It should be noted that during hemodialysis, the amount of dehydration has a direct impact on the blood pressure of the patient. If hemodialysis is carried out with an over-estimated dehydration amount, the patient may be dehydrated, resulting in sudden drop of blood pressure and physical discomfort. If hypotension occurs frequently, the course of hemodialysis will be forced to end early or stop, which will lead to insufficient removal of urine toxins over time. On the other hand, if hemodialysis is carried out with an under-estimated dehydration amount, the patient will be in a condition of high body fluid for a long time, and hypertension and ventricular hypertrophy will easily occur. Therefore, setting an ideal dehydration amount has always been a very important issue. In the past, medical staff mostly used a trial-and-error method to determine the amount of dehydration, thus generally needing a lot of experience to estimate the ideal dehydration amount. Moreover, different patients have different physical conditions, and when the condition of the patient is unstable, professional judgment and real-time monitoring of medical personnel are required, thus increasing the medical cost. In addition, there are still many dialysis patients who need to take blood pressure control drugs to stabilize blood pressure after hemodialysis. All of these show that there is still considerable room for improvement in blood pressure control and ideal dehydration amount setting. Therefore, how to estimate the ideal dehydration amount to reduce the discomfort of patients and reduce the medical cost is a subject for those skilled in the art.

SUMMARY

The disclosure provides a dehydration amount prediction method for hemodialysis and an electronic device using the same, which can automatically provide an ideal dehydration amount, thereby reducing the burden on medical personnel and the discomfort of a patient.

An embodiment of the invention provides a dehydration amount prediction method for hemodialysis, and the method includes the following steps. Physiological data and hemodialysis treatment data of a first patient are obtained. The first patient is determined to belong to one of groups, where the groups are respectively associated with a plurality of prediction models. A target prediction model corresponding to the one of the groups is selected from the prediction models. The physiological data and the hemodialysis treatment data are provided to the target prediction model to generate a recommended dehydration amount by the target prediction model.

An embodiment of the invention provides an electronic device, which includes a storage circuit and a processor. The storage circuit stores a plurality of modules, and the processor is coupled to the storage circuit. The processor is configured to access the module to perform the following steps. Physiological data and hemodialysis treatment data of a first patient are obtained. The first patient is determined to belong to one of groups, where the groups are respectively associated with a plurality of prediction models. A target prediction model corresponding to the one of the groups is selected from the prediction models. The physiological data and the hemodialysis treatment data are provided to the target prediction model to generate a recommended dehydration amount by the target prediction model.

Based on the above, in the embodiments of the invention, a group to which a patient belongs is determined first, and then a corresponding target prediction model is determined according to the group to which the patient belongs. Then, after physiological data and hemodialysis treatment data of the patient are given to the target prediction model, the target prediction model can automatically generate an ideal recommended dehydration amount. Therefore, a dialysis machine can refer to the recommended dehydration amount generated by the target prediction model for dehydration amount parameter setting. In this way, the medical cost for medical staff to manually evaluate the dehydration amount can be reduced, and the discomfort of patients caused by a hemodialysis treatment course can be reduced.

In order to make the aforementioned features and advantages of the invention comprehensible, embodiments accompanied with figures are described in detail below.

DESCRIPTION OF THE EMBODIMENTS

Some embodiments of the invention will be described in detail next with reference to the accompanying drawings.

Component symbols referred to in the following description will be regarded as the same or similar components when the same component symbols appear in different drawings. These embodiments are only a part of the invention, and not all possible embodiments of the invention are disclosed. More specifically, these embodiments are merely examples of methods and devices within the scope of the patent application of the invention.

Figure 1:
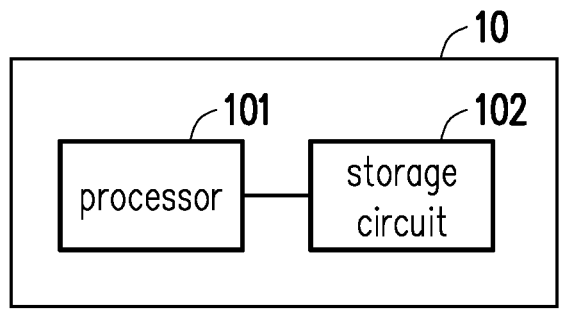
FIG. 1 is a block diagram of an electronic device according to an embodiment of the invention.

FIG. 1 is a block diagram of an electronic device according to an embodiment of the invention. However, this is for convenience of explanation only and is not intended to limit the invention. First of all, FIG. 1 first introduces all components and configuration relationships in the electronic device. Detailed functions will be disclosed together with FIG. 2 and FIG. 3.

Referring to FIG. 1, an electronic device 10 is applied to a hemodialysis process and is used to estimate a recommended dehydration amount set for hemodialysis of a patient. The electronic device 10 includes a processor 101 and a storage circuit 102.

The storage circuit 102 is configured to store data, software modules and codes, which may be, for example, any type of fixed or removable random access memory (RAM), read-only memory (ROM), flash memory, hard disk or other similar devices, integrated circuits, and a combination thereof.

The processor 101 is configured to execute a proposed dehydration amount prediction method, which may be, for example, a central processing unit (CPU), a graphics processing unit (GPU), or another programmable general-purpose or special-purpose microprocessor, digital signal processor (DSP), programmable controllers, application specific integrated circuit (ASIC), or programmable logic device (PLD), or another similar device, chip or integrated circuit, or a combinations thereof. In an embodiment, the processor 101 can load a code or module recorded in the storage circuit 102 to execute the dehydration amount prediction method proposed in the embodiment.

In an embodiment, the electronic device 10 may be a hemodialysis machine, a control instrument, a computer device having a computing function, a server device, or an electronic device integrating the above devices. The invention does not limit the type of the electronic device 10.

Figure 2:
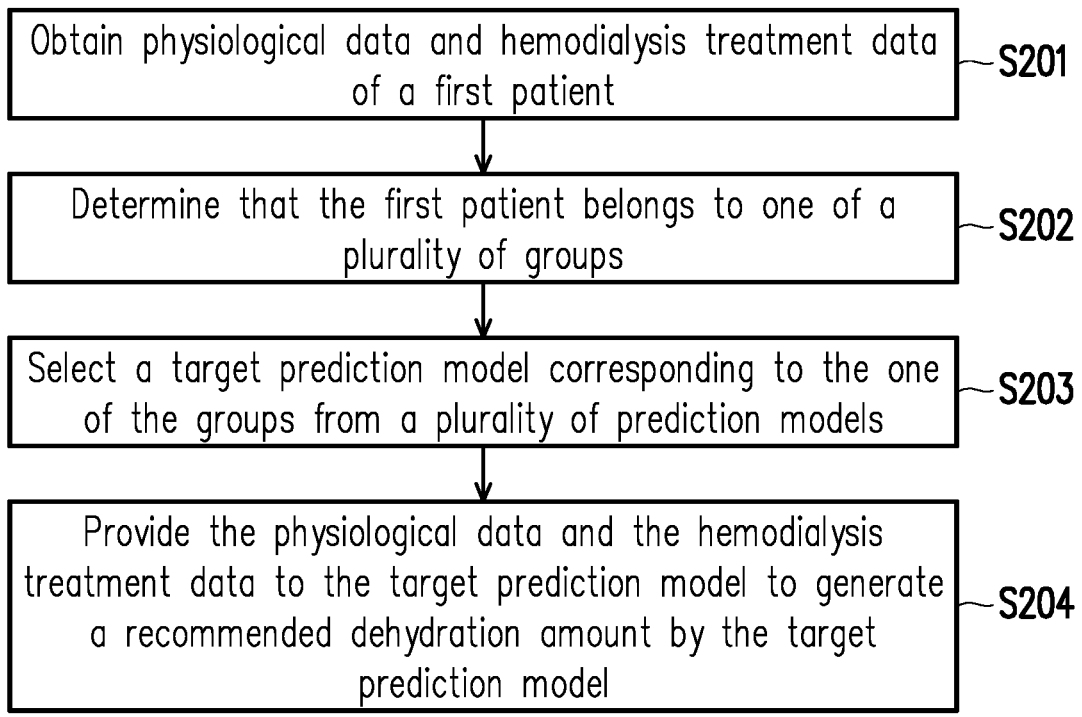
FIG. 2 is a flowchart of a dehydration amount prediction method for hemodialysis according to an embodiment of the invention.

FIG. 2 is a flowchart of a dehydration amount prediction method for hemodialysis according to an embodiment of the invention. Please refer to FIG. 1 and FIG. 2. The method of the present embodiment is applicable to the electronic device 10 in the above embodiment. The detailed steps of the dehydration amount prediction method for hemodialysis in the present embodiment will be described below in conjunction with various components in the electronic device 10.

In step S201, the processor 101 acquires physiological data and hemodialysis treatment data of a patient (i.e., a first patient). The above physiological data may include basic data of the patient, personal medical history data of the patient or physiological evaluation data of the patient measured before hemodialysis, or the like. The hemodialysis treatment data refers to data related to a previous hemodialysis treatment course or courses of the patient, which may include a blood pressure value during hemodialysis, a set dehydration amount and an actual dehydration amount for hemodialysis, or other parameters for hemodialysis.

In detail, after the patient checks in a medical institution or a kidney dialysis center, medical staff perform physiological measurement, which may include weight measurement, blood pressure measurement and the like, on the patient, and input the physiological data of the patient through an input interface (not shown) of the electronic device 10 to obtain the physiological data of the patient before hemodialysis (e.g., weight and blood pressure values before hemodialysis), where the input interface is, for example, a keyboard, a mouse, a voice input device or a touch device, or the like, so that the medical staff can input the measured physiological data of the patient to the electronic device 10. In another embodiment, the electronic device 10 is further provided with a wireless or wired data transmission interface (not shown) which can be connected to a physiological data measuring instrument and receive the physiological data of the patient from the physiological data measuring instrument connected thereto. The aforementioned physiological data measuring instrument is, for example, a sphygmomanometer, a weight meter or a wearable measuring device (such as a 24-hour blood pressure measuring device, a smart watch capable of measuring blood pressure or heart rate, a smart shoe capable of measuring weight, and the like) worn by the patient, and the processor 101 can obtain the physiological data of the patient through the data transmission interface. Further, the aforementioned data transmission interface may adopt wireless Bluetooth transmission, ZigBee transmission, Wifi transmission, etc., or wired Ethernet transmission, USB interface transmission, thunderbolt interface transmission, etc., and is not limited by the invention. Further, a patient data management center of the medical institution or hemodialysis center also stores the basic data of the patient, such as gender, age, dialysis years and diabetes status. Further, the patient data management center of the medical institution or hemodialysis center also stores the hemodialysis treatment data of the patient. Based on this, the processor 101 can obtain the basic data of the patient from the patient data management center and related data of the previous hemodialysis course through the storage circuit 102 or a communication circuit (not shown), and obtain the physiological evaluation data generated by the physiological measurement of the patient with a measuring instrument before hemodialysis, so as to obtain the physiological data of the patient.

In step S202, the processor 101 determines that the first patient belongs to one of a plurality of groups. In step S203, the processor 101 selects a target prediction model corresponding to the one of the plurality of groups from a plurality of prediction models. Specifically, in an embodiment of the invention, a plurality of prediction models are generated according to machine learning algorithm training. The plurality of groups is respectively associated with the plurality of prediction models, that is, different groups correspond to different prediction models. Therefore, the patient is determined by the processor 101 to belong to one of the plurality of groups according to the physiological characteristic thereof, and then the processor 101 uses the corresponding prediction model to estimate a recommended dehydration amount of the patient. In other words, for different patients, the processor 101 may use different prediction models to estimate the dehydration amount.

In detail, the physiological characteristic of the patient is a reference factor for setting the dehydration amount, which may be blood pressure or other types of data, and may be designed according to clinical manifestations. In an embodiment, the processor 101 can digitize the physiological characteristic of the patient into a physiological characteristic factor through the physiological data and the hemodialysis treatment data of the patient obtained in step S201, patients with similar physiological characteristic factors are classified into the same group, and historical physiological data and historical hemodialysis treatment data of the patients in the same group are used as training data to train a prediction model. Therefore, the patients with similar physiological characteristics in the same group use the same prediction model to estimate the recommended dehydration amount. Subsequent embodiments will clearly explain the construction of the prediction models.

It should be noted that in an embodiment, in the process of constructing a plurality of prediction models, a patient classification action based on physiological characteristics has been performed to establish the plurality of prediction models corresponding to different groups. Therefore, a group index of each patient can also be given in the process of constructing the plurality of prediction models, so that the processor 101 can directly select a corresponding target prediction model according to the group index of the patient before hemodialysis on the patient, without the need to perform patient classification again according to a huge amount of patient data. More specifically, in the process of constructing the prediction models, a patient can be assigned a group index because the patient is classified into a group based on the physiological characteristic, so the processor 101 can directly know the group to which the patient belongs according to the group index corresponding to the patient and obtain the corresponding target prediction model accordingly. Examples are as follows: the patient is assumed to be classified into a first group, and the patient may be given a group index of 'index_1'; and the patient is assumed to be classified into a second group, and the patient may be given a group index of 'index_2'. Therefore, the processor 101 can directly determine the group to which the patient belongs according to the group index.

After determining the group to which the patient belongs and the corresponding target prediction model, in step S204, the processor 101 provides the physiological data and the hemodialysis treatment data to the target prediction model to generate the recommended dehydration amount by the target prediction model. Specifically, the processor 101 can input the physiological data and the hemodialysis treatment data of the patient into the pre-established target prediction model, and generate the recommended dehydration amount by the target prediction model. Here, the recommended dehydration amount may include a total recommended dehydration amount and a recommended dehydration amount per hour. The processor 101 can then display the recommended dehydration amount on a display interface for reference by medical personnel, or the processor 101 can set the instrument parameters of an electronic medical device (i.e., dialysis instrument) according to the recommended dehydration amount.

In one embodiment, the processor 101 can further calculate the dehydration amount per hour according to the recommended dehydration amount and preset dialysis time, and display the dehydration amount per hour on the display interface. For example, it is assumed that the recommended dehydration amount is X ml and the preset dialysis time is four hours, and the dehydration amount per hour is X/4 ml. In addition, the processor 101 can obtain the actual dehydration amount of the patient during hemodialysis from the dialysis instrument, and monitor whether the actual dehydration amount during hemodialysis by the dialysis instrument reaches the recommended dehydration amount or the dehydration amount per hour, so that medical staff can make appropriate treatment according to a monitoring result. In addition, the processor 101 further records the actual dehydration amount, which can be used as training data for training the prediction models.

Figure 3:
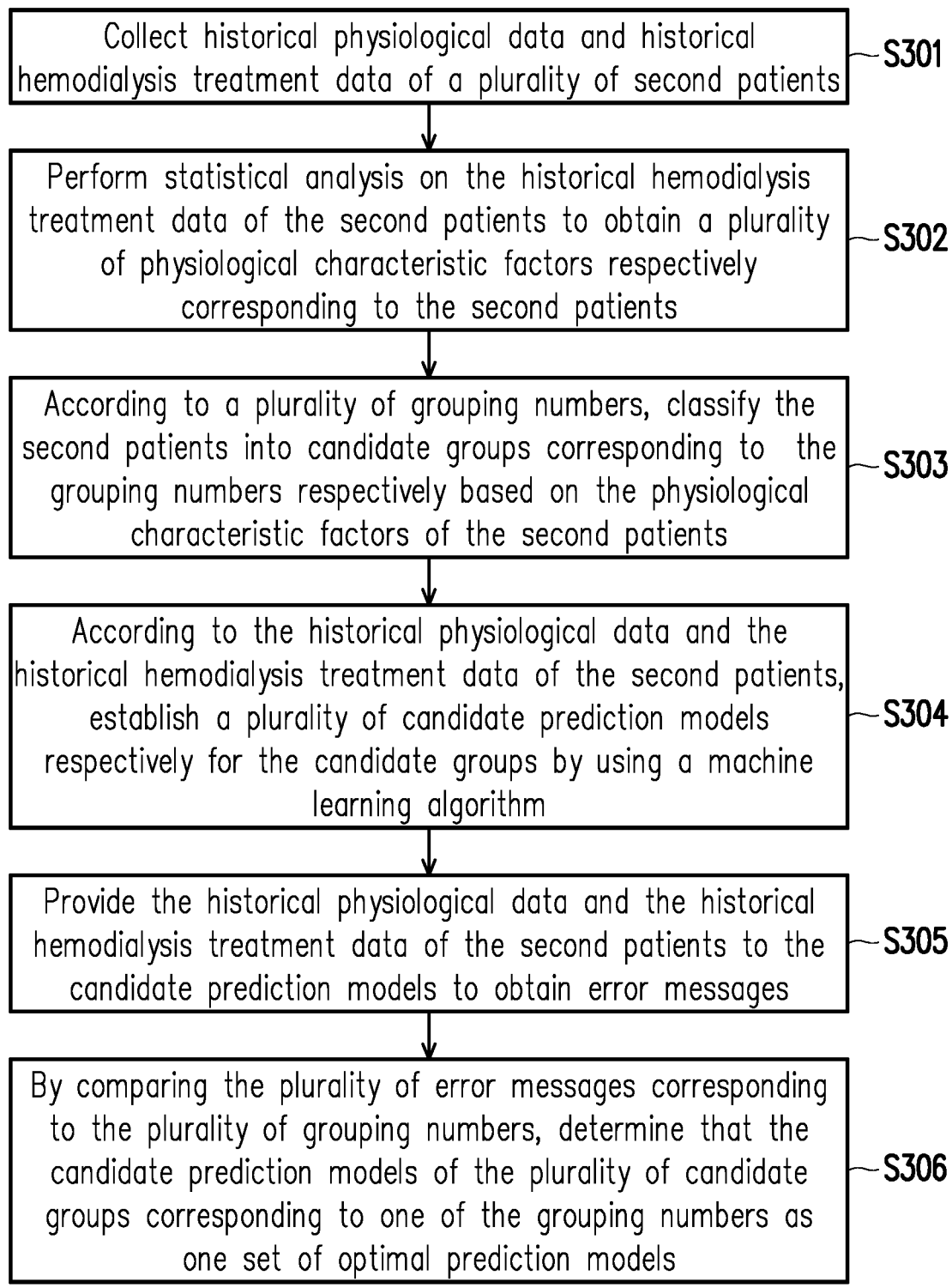
FIG. 3 is a flowchart of a dehydration amount prediction method for hemodialysis according to an embodiment of the invention.

The following will further explain the implementation of classifying patients and then constructing the prediction models. FIG. 3 is a flowchart of a dehydration amount prediction method for hemodialysis according to an embodiment of the invention. Please refer to FIG. 1 and FIG. 3. The method of the present embodiment is applicable to the electronic device 10 in the above embodiment. The detailed steps of the dehydration amount prediction method for hemodialysis in the present embodiment will be described below in conjunction with various components in the electronic device 10. It should be noted that the process shown in FIG. 3 for establishing the prediction models is executed before the process shown in FIG. 2 for estimating the recommended dehydration amount using the prediction models, and the first patient mentioned in FIG. 2 is one of second patients mentioned in FIG. 3.

In step S301, the processor 101 collects historical physiological data and historical hemodialysis treatment data of a plurality of second patients. For example, the processor 101 can collect the historical physiological data and the historical hemodialysis treatment data of all the second patients in the past two months from the storage circuit 102 or/and through the data transmission interface. Generally speaking, hemodialysis patients need to undergo hemodialysis three times a week. After each hemodialysis, pre-dialysis physiological evaluation data, basic data and current hemodialysis treatment data of the patients are stored in the patient data management center to form the historical physiological data and the historical hemodialysis treatment data. Therefore, the processor 101 can collect the historical physiological data and the historical hemodialysis treatment data of all the second patients from the patient data management center through the wireless or wired data transmission interface. For example, the historical physiological data may include weight, blood pressure value, gender, age, diabetes state, dialysis years and the like corresponding to each hemodialysis in the past two months. The historical hemodialysis treatment data may include dialysis parameter settings and dehydration amount settings corresponding to each hemodialysis in the past two months, blood pressure values during the dialysis process, and the like.

In step S302, the processor 101 performs statistical analysis on the historical hemodialysis treatment data of the plurality of second patients to obtain a plurality of physiological characteristic factors respectively corresponding to the plurality of second patients. The above statistical analysis can be linear regression analysis, factor analysis or other types of statistical analysis. For each second patient, the processor 101 can extract data associated with specific physiological characteristics from the historical hemodialysis treatment data, and perform statistical analysis on the basis of the extracted data to generate corresponding physiological characteristic factors. In one embodiment, if the above statistical analysis is linear regression analysis, the physiological characteristic factor may be a regression coefficient generated by performing linear regression analysis on the historical hemodialysis treatment data. Alternatively, the physiological characteristic factor may be an average value generated by performing statistical averaging on the historical hemodialysis treatment data.

After generating the physiological characteristic factors of each second patient, in step S303, the processor 101 classifies, according to a plurality of grouping numbers, the plurality of second patients respectively into a plurality of candidate groups corresponding to the grouping numbers based on the physiological characteristic factors of the plurality of second patients. Specifically, it is assumed that the grouping numbers may be 2, 3 and 4 respectively, and the processor 101 can classify the plurality of second patients into 4 candidate groups, 3 candidate groups and 2 candidate groups respectively according to the physiological characteristic factors of the plurality of second patients and the three grouping numbers. Specifically, the physiological characteristic factor may be a regression coefficient generated by performing regression statistical analysis on the physiological data of the second patients. The processor 101 compares the physiological characteristic factors of the second patients with a threshold value according to the grouping number "2", so as to group the second patients into two candidate groups. The processor 101 compares the physiological characteristic factors of the second patients with two threshold values according to the grouping number "3", so as to group the second patients into three candidate groups. The processor 101 compares the physiological characteristic factors of the second patients with three threshold values according to the grouping number "4", so as to group the second patients into four candidate groups. These threshold values can be quartiles generated by making statistics on the physiological characteristic factors of all the second patients.

In addition, these candidate groups have corresponding group indexes respectively. In response to the processor 101 classifying each second patient into a corresponding candidate group, the processor 101 assigns each second patient one of the plurality of group indexes. Thus, the processor 101 can determine that the first patient belongs to the one of the groups according to one of the group indexes associated with the first patient to be dialyzed (i.e., one of the second patients used for establishing the prediction models).

After classifying the plurality of second patients, in step S304, the processor 101, according to the historical physiological data and the historical hemodialysis treatment data of the second patients, establishes candidate prediction models corresponding to each candidate group by using a machine learning algorithm for each candidate group corresponding to each grouping number. In other words, in response to the plurality of second patients being classified into the plurality of candidate groups, the historical physiological data and the historical hemodialysis treatment data of the plurality of second patients are also correspondingly classified into a plurality of training data sets, and each training data set corresponds to one candidate group, so that the processor 101 can respectively train a plurality of candidate prediction models by using the machine learning algorithm according to the plurality of training data sets. It can be seen that each candidate prediction model corresponds to one candidate group in a one-to-one mode. That is, the grouping numbers are assumed to be 2, 3 and 4 respectively, and the processor 101 can obtain 9 candidate groups and correspondingly generate 9 candidate prediction models.

Further, the processor 101 uses the historical dehydration amount in the historical hemodialysis treatment data, the historical physiological data and the historical hemodialysis treatment data of a plurality of second patients in a candidate group as training data sets of a supervised learning algorithm to establish a candidate prediction model corresponding to one candidate group. More specifically, the processor 101 can take the historical dehydration amount in the historical hemodialysis treatment data as expected output in the supervised learning algorithm, and take the historical physiological data and other historical hemodialysis treatment data of the plurality of second patients in the same candidate group as input objects in the supervised learning algorithm, so as to train a candidate prediction model corresponding to one candidate group and capable of predicting the recommended dehydration amount. The above supervised learning algorithm includes, for example, a multiple linear regression (MLR) algorithm. The supervised learning algorithm is assumed to be multiple linear regression, and the processor 101 can take the historical dehydration amount in the historical hemodialysis treatment data as a dependent variable of multiple linear regression, and take other historical physiological data and other historical hemodialysis treatment data of the plurality of second patients as an independent variable of multiple linear regression to generate a linear regression model. In addition, the processor 101 can further use a stepwise selection method to screen out important independent variables for establishing the prediction models.

Then, in step S305, the processor 101 provides the historical physiological data and the historical hemodialysis treatment data of the second patients to each candidate prediction model to obtain a plurality of error messages. In step S306, the processor 101 determines the candidate prediction models of the candidate groups corresponding to one of the plurality of grouping numbers as a set of optimal prediction models by comparing the plurality of error messages corresponding to the plurality of grouping numbers, where the plurality of prediction models of the plurality of groups actually used for dehydration amount estimation in steps S202-S203 are the optimal prediction models. That is, the processor 101 can perform model verification on a plurality of candidate groups corresponding to each grouping number. In one embodiment, the processor 101 calculates a first error message for 2 candidate prediction models of 2 candidate groups corresponding to the grouping number 2, calculates a second error message for 3 candidate prediction models of 3 candidate groups corresponding to the grouping number 3, and calculates a third error message for 4 candidate prediction models of 4 candidate groups corresponding to the grouping number 4. The processor 101 selects a set of optimal prediction models by comparing the first error message, the second error message and the third error message, for example, selects one with the smallest average error from the first error message, the second error message and the third error message, and determines that the plurality of candidate prediction models of the plurality of candidate groups corresponding to the error message with the smallest average error value as the set of optimal prediction models.

In another embodiment, based on the classification of the candidate groups corresponding to one of the grouping numbers, the processor 101 can input the historical physiological data and the historical hemodialysis treatment data of the plurality of second patients one by one to a plurality of first candidate prediction models corresponding to the first candidate group, generate a plurality of error values by comparing the prediction outputs of the plurality of first candidate prediction models with actual data (i.e., the historical dehydration amount in the historical hemodialysis treatment data), and then average absolute values of the error values to generate a model average absolute error associated with the first prediction model as the first error message. Similarly, the processor 101 can also obtain a model average absolute error of a plurality of second candidate prediction models corresponding to another one of the grouping numbers in a similar manner as the second error message. In this way, by comparing the first error message with the second error message, the processor 101 can obtain a plurality of first candidate prediction models with a smaller error as a set of optimal prediction models, and generate the recommended dehydration amount according to the set of optimal prediction models for reference by medical personnel.

In one embodiment, after a preset period of time (e.g., 2 months), the processor 101 can further reclassify the second patients into a plurality of candidate groups corresponding to a plurality of grouping numbers according to the currently collected historical physiological data and historical hemodialysis treatment data of the second patients, and retrain the candidate prediction models for the candidate groups by using the machine learning algorithm. In other words, steps S301-S306 in FIG. 3 can be executed every other preset period of time to retrain the prediction models. Thus, it can be seen that the classification of patients is also performed every other preset period of time.

Figure 4:
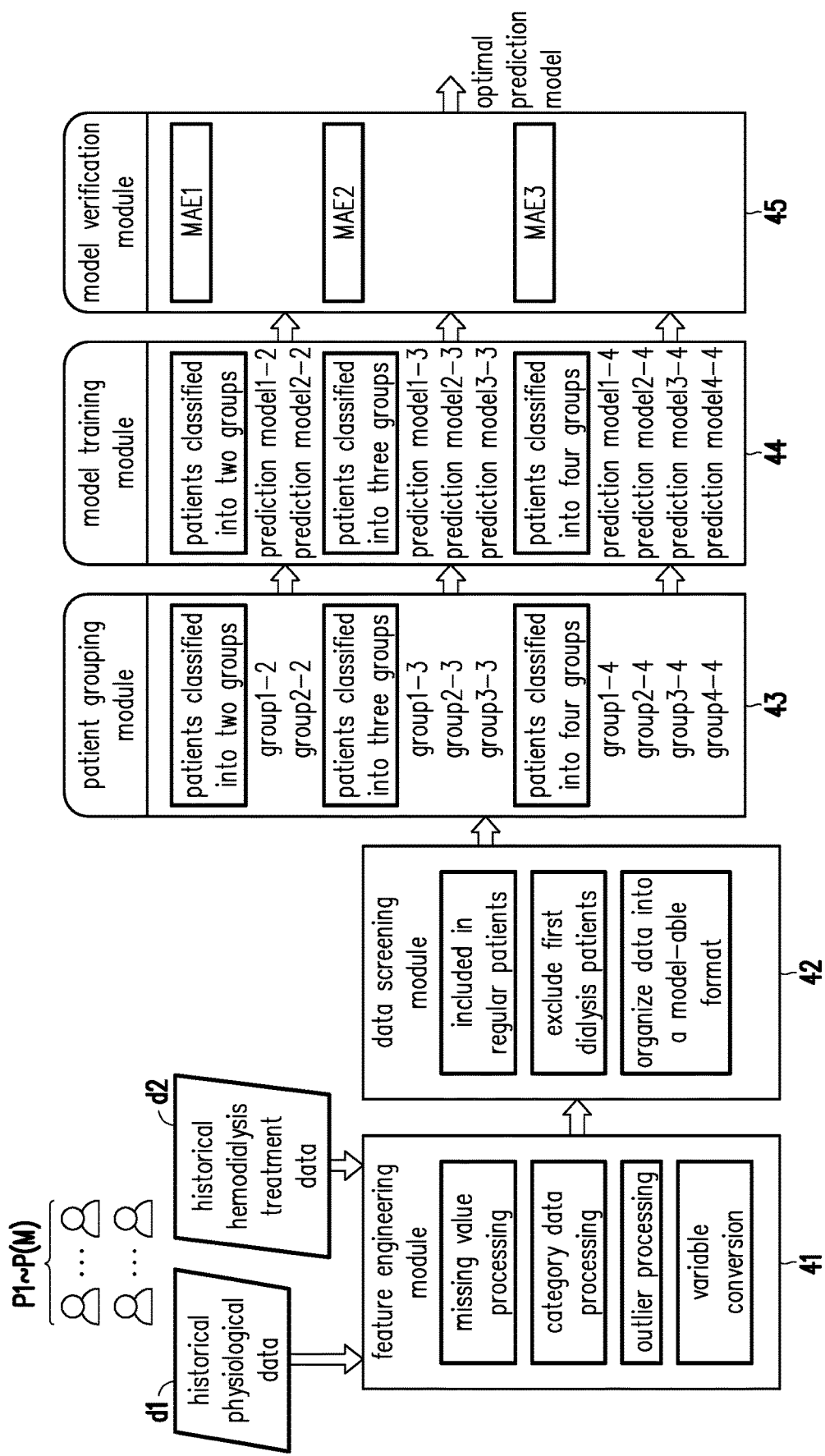
FIG. 4 is a detailed schematic diagram of model construction according to an embodiment of the invention

FIG. 4 is a detailed schematic diagram of model construction according to an embodiment of the invention. An example shown in FIG. 4 uses a feature engineering module 41, a data screening module 42, a patient grouping module 43, a model training module 44 and a model verification module 45 to generate an optimal prediction model for predicting the recommended dehydration amount. The feature engineering module 41, the data screening module 42, the patient grouping module 43, the model training module 44, and the model verification module 45 can be implemented by software components recorded by the processor 101 and the storage circuit 102.

Referring to FIG. 4, the feature engineering module 41 can obtain historical physiological data d1 and historical hemodialysis treatment data d2 of a plurality of patients P1-P(M) from the patient data management center of the medical institution. The feature engineering module 41 performs missing value processing, category data processing, outlier processing and variable conversion on the historical physiological data d1 and the historical hemodialysis treatment data d2. Then, the data screening module 42 excludes the patients undergoing dialysis for the first time from the patients P1-P(M), so that only relevant data of regular patients are included in the training data for constructing the prediction models. Specifically, the time for first dialysis on first dialysis patients is 2 hours, different from the complete dialysis time for regular patients, which is 4 hours. In addition, the body of the first dialysis patients is still in an adaptive state, so the referential value of their physiological data is low. In other words, the relevant data of the first dialysis patients are not suitable for inclusion in the training data for establishing the prediction models. The data screening module 42 finally sorts the screened historical physiological data d1 and historical hemodialysis treatment data d2 into a data format suitable for establishing the prediction models by the machine learning algorithm. Generally speaking, before training the prediction models according to the machine learning algorithm, the feature engineering module 41 and the data screening module 42 perform data sorting on the historical physiological data d1 and the historical hemodialysis treatment data d2 to improve the accuracy of the prediction models.

Then, the patient grouping module 43 classifies the regular patients in the patients P1-P(M) into 2 candidate groups, 3 candidate groups and 4 candidate groups respectively according to the three grouping numbers "2", "3" and "4" with three different classification methods. When the regular patients in the patients P1-P(M) are classified into 2 groups, the regular patients are classified into a group 1-2 and a group 2-2. When the regular patients in the patients P1-P(M) are classified into 3 groups, the regular patients are classified into a group 1-3, a group 2-3 and a group 3-3. When the regular patients in the patients P1-P(M) are classified into 4 groups, the regular patients are classified into a group 1-4, a group 2-4, a group 3-4 and a group 4-4. Classification according to the physiological characteristic factors of the patients has been described in the previous embodiments.

In particular, based on clinical observation, patients with similar blood pressure variation trends during hemodialysis have similar physiological and clinical manifestations in terms of the influence on the dehydration amount. Based on this, in the embodiment, by performing statistical analysis on the historical hemodialysis treatment data, the patient grouping module 43 can analyze the blood pressure variation trend (i.e., a physiological characteristic) of patients during hemodialysis treatment to classify the patients according to the blood pressure variation trend of each patient.

Specifically, the patient grouping module 43 can obtain a plurality of blood pressure values corresponding to different time points in a plurality of previous hemodialysis processes from the historical hemodialysis treatment data of the patients. The patient grouping module 43 can perform regression analysis on the blood pressure values corresponding to different time points to generate a plurality of blood pressure variation trend factors (i.e., a physiological characteristic factor) of the patients. Here, the blood pressure variation trend factors of the multiple patients are multiple regression coefficients generated based on regression analysis. In detail, for each regular patient, the patient grouping module 43 can take the time points in the dialysis treatment process as the independent variable of regression analysis, and take the blood pressure values corresponding to the time points in the dialysis treatment process as the dependent variable of regression analysis to generate a linear regression equation. A coefficient of a first term of the linear regression equation is a regression coefficient (also known as regression straight line slope) which can be used as the blood pressure variation trend factor, and can indicate the magnitude of blood pressure change and the direction of blood pressure change. In other words, by making statistics on the blood pressure values in the past hemodialysis processes, the patient grouping module 43 can obtain the blood pressure variation trend of each patient in the hemodialysis process, such as sudden drop of blood pressure, slow drop of blood pressure, stable blood pressure, rise of blood pressure, etc., so as to classify the patients according to the blood pressure variation trend of the regular patients in the patients P1-P(M).

Figure 5:
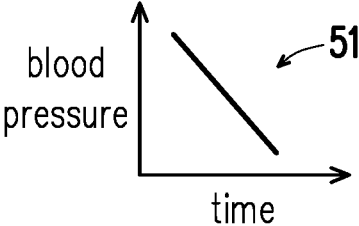
FIG. 5 is a schematic diagram illustrating classification according to blood pressure variation trends according to an embodiment of the invention.
Figure 5:
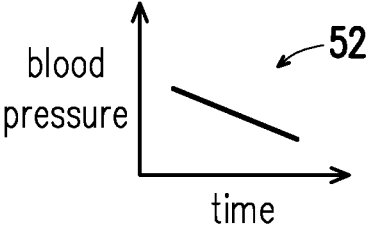
Figure 5:
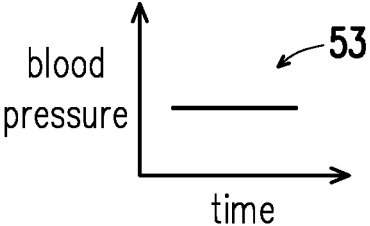
Figure 5:
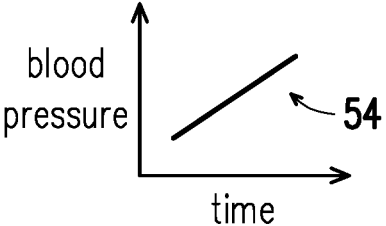

For example, FIG. 5 is a schematic diagram illustrating classification according to blood pressure variation trends according to an embodiment of the invention. Referring to FIG. 5, the blood pressure variation trend factor of a patient A is assumed to be less than a threshold value Q1, then the patient A is classified into the group 1-4, and the blood pressure variation trend thereof is substantially similar to that shown in a graph 51. The graph 51 shows that the blood pressure variation trend of the patients in the group 1-4 decreases significantly during dialysis. The blood pressure variation trend factor of a patient B is assumed to be greater than the threshold value Q1 but less than a threshold value Q2, then the patient B is classified into the group 2-4, and the blood pressure variation trend thereof is substantially similar to that shown in a graph 52. The graph 52 shows that the blood pressure variation trend of the patients in the group 2-4 decreases slightly during dialysis. The blood pressure variation trend factor of a patient C is assumed to be greater than the threshold value Q2 but less than a threshold value Q3, then the patient C is classified into the group 3-4, and the blood pressure variation trend thereof is substantially similar to that shown in a graph 53. The graph 53 shows that the blood pressure variation trend of the patients in group 3-4 is relatively stable during dialysis. The blood pressure variation trend factor of a patient D is assumed to be greater than the threshold value Q3, then the patient D is classified into the group 4-4, and the blood pressure variation trend thereof is substantially similar to that shown in a graph 54. The graph 54 shows that the blood pressure variation trend of the patients in the group 4-4 increases during dialysis. The patients in the above four groups 1-4, 2-4, 3-4 and 4-4 have different needs for the dehydration amount due to the different blood pressure variation trends. In another embodiment, the above threshold values Q1 to Q3 can be set as quartiles of the regression coefficient distribution of all blood pressure variation trends, and can be adjusted as required in other embodiments, without being limited thereto.

Returning to FIG. 4, after the patient grouping module 43 classifies the regular patients, the model training module 44 can establish candidate prediction models one by one for the candidate groups. The model training module 44 can establish a prediction model 1-2 and a prediction model 2-2 for a group 1-2 and a group 2-2 respectively according to the machine learning algorithm; establish a prediction model 1-3, a prediction model 2-3 and a prediction model 3-3 for a group 1-3, a group 2-3 and a group 3-3 respectively according to the machine learning algorithm; and establish a prediction model 1-4, a prediction model 2-4, a prediction model 3-4 and a prediction model 4-4 for a group 1-4, a group 2-4, a group 3-4 and a group 4-4 respectively according to the machine learning algorithm. For example, the model training module 44 can train the prediction model 1-2 according to historical physiological data and historical hemodialysis treatment data of patients in the group 1-2, and train the prediction model 2-2 according to historical physiological data and historical hemodialysis treatment data of patients in the group 2-2. In an example of FIG. 4, the model training module 44 can use the MLR algorithm to train three groups of prediction models, nine in total. For example, Table 1 is an example of the prediction model 1-4, the prediction model 2-4, the prediction model 3-4 and the prediction model 4-4 generated based on the MLR algorithm.

TABLE 1

| prediction model 1-4 | $f(x) = a_0 + a_1 b_1 + a_2 b_2 + a_3 b_3$ |
| prediction model 2-4 | $f(x) = c_0 + c_1 b_1 + c_2 b_2 + c_3 b_3$ |
| prediction model 3-4 | $f(x) = d_0 + d_1 b_1 + d_2 b_2 + d_3 b_3$ |
| prediction model 4-4 | $f(x) = e_0 + e_1 b_1 + e_2 b_2 + e_3 b_3$ |

In Table 1, $a_0$, $a_1$, $a_2$, $a_3$, $c_0$, $c_1$, $c_2$, $c_3$, $d_0$, $d_1$, $d_2$, $d_3$, $e_0$, $e_1$, $e_2$ and $e_3$ are trained model parameters. $b_1$ is the age of the patients. $b_2$ is the body weight of the patients after previous dialysis. $b_3$ is the total dehydration amount in previous dialysis. However, Table 1 is merely an exemplary illustration and is not intended to limit the invention.

Next, the model verification module 45 performs model verification on each set of candidate prediction models generated by the model training module 44. The model verification module 45 can obtain a model average absolute error MAE1 of the prediction model 1-2 and the prediction model 2-2 corresponding to the same grouping number "2". The model verification module 45 can obtain a model average absolute error MAE2 of the prediction model 1-3, the prediction model 2-3 and the prediction model 3-3 corresponding to the same grouping number "3". The model verification module 45 can obtain a model average absolute error MAE3 of the prediction model 1-4, the prediction model 2-4, the prediction model 3-4 and the prediction model 4-4 corresponding to the same grouping number "4". Therefore, by comparing the model average absolute error MAE1, the model average absolute error MAE2 and the model average absolute error MAE3, the model verification module 45 can determine a set of optimal prediction models according to the minimum value in the three model average absolute errors.

For example, if the model verification module 45 finds that the model average absolute error MAE3 is the smallest, the model verification module 45 determines that the prediction model 1-4, the prediction model 2-4, the prediction model 3-4 and the prediction model 4-4 are the optimal prediction models. Based on this, when a patient checks in the medical institution or the kidney dialysis center, the electronic device 10 in the embodiment of the invention determines which of the group 1-4, the group 2-4, the group 3-4 and the group 4-4 the patient is classified into. If the electronic device 10 determines that the patient is classified into the group 1-4, the electronic device 10 can use the prediction model 1-4 to predict the recommended dehydration amount of the patient during hemodialysis this time. According to the example shown in Table 1, the electronic device 10 obtains physiological data (i.e., the age of the patient) and hemodialysis treatment data (i.e., body weight after previous dialysis and a total dehydration amount during previous dialysis) of the patient from the patient data management center. It is assumed that the patient is 65 years old, the body weight after previous dialysis is 56 kg, and the total dehydration amount during previous dialysis is 2.4 kg, and it is assumed that $a_0$, $a_1$, $a_2$ and $a_3$ are −0.32, −1.5, 1.2 and 13.8 respectively in sequence, the recommended dehydration amount during dialysis this time is −0.32−1.5*65+1.2*56+13.8*2.4=2.5 (kg). Based on this, the electronic device 10 can provide a total recommended dehydration amount of 2.5 kg and a recommended dehydration amount per hour of 2.5/4=0.625 kg. Therefore, medical personnel can set the hemodialysis instrument with reference to the recommended dehydration amount provided by the electronic device 10. In another embodiment, the electronic device 10 sets the parameters of the hemodialysis instrument used by the patient, monitors whether the hemodialysis instrument used by the patient reaches the recommended dehydration amount per hour, further monitors whether the hemodialysis instrument used by the patient reaches the total recommended dehydration amount, and records the actual dehydration amount accordingly for use in the next retraining.

It is worth mentioning that the feature engineering module 41, the data screening module 42, the patient grouping module 43, the model training module 44 and the model verification module 45 can periodically retrain the prediction models to ensure that parameters of the prediction models can be adaptively changed along with the changes in the physiological state of the patients, thus maintaining the stability of the prediction models. For example, the feature engineering module 41, the data screening module 42, the patient grouping module 43, the model training module 44 and the model verification module 45 can retrain a set of optimal prediction models based on the historical data of the past few months at predetermined intervals, such as every other month. From this, it can be seen that in the process of retraining the prediction models with the change of the physical condition of the patients, the patients may be classified into other groups and the prediction model corresponding to another group may be used, so that the physical needs of the patients can be better met. Taking FIG. 5 as an example, the patient A may be classified into the group 3-4 at present, but will be classified into the group 2-4 one month later.

It should be noted that in the embodiments, the grouping numbers of groups can be adjusted according to actual needs, and are not limited by the invention. In addition, the invention does not limit model parameters or parameter weights of the prediction models, which depend on actual training results. For example, prediction models trained at different time points may use different model parameters or different parameter weights. With the accumulation of data, the prediction models can be more consistent with the actual needs of the patients.

To sum up, in the embodiments, the historical physiological data and the historical hemodialysis treatment data of the patients are divided into a plurality of training data sets, so as to train corresponding prediction models for a plurality of groups respectively. Correspondingly, before the patients undergo hemodialysis, the corresponding target prediction model can be determined according to which group the patients belong to, so as to automatically generate an ideal recommended dehydration amount according to the target prediction model. Based on this, for the same group of patients with similar clinical manifestations in terms of the influence on the dehydration amount, the same prediction model can be used to predict the recommended dehydration amount, which ensures the accuracy of dehydration amount setting, so as to stabilize the blood pressure of patients during dialysis and after dialysis, thus reducing discomfort symptoms caused by dialysis treatment and reducing the occurrence probability of cardiovascular diseases. Furthermore, by automatically retrieving the physiological data and hemodialysis treatment data of patients and using the target prediction model to make automatic prediction, the medical cost of manually evaluating the dehydration amount by medical personnel can be reduced, and considerable assistance can be provided to less experienced medical personnel.

Although the invention has been disclosed by way of embodiments as above, they are not intended to limit the invention. Those of ordinary skill in the art can make some changes and modifications without departing from the spirit and scope of the invention. Therefore, the scope of protection of the invention is to be determined by the scope of the appended claims.

What is claimed is:

1. A dehydration amount prediction method for hemodialysis, the method comprising:
performing following through an electronic device:
constructing a plurality of prediction models associated with a plurality of groups respectively, including:
using a feature engineering module to obtain historical physiological data and historical hemodialysis treatment data of a plurality of patients;
using a grouping module to perform statistical analysis on the historical hemodialysis treatment data to obtain a plurality of physiological characteristic factors corresponding to the patients respectively;
using the grouping module to classify the patients into a plurality sets of candidate groups corresponding to a plurality of grouping numbers respectively based on the physiological characteristic factors;
using a model training module to establish a plurality of candidate prediction models respectively for all of the candidate groups by using a machine learning algorithm according to the historical physiological data and the historical hemodialysis treatment data of the patients;
using a model verification module to provide the historical physiological data and the historical hemodialysis treatment data of the patients to the candidate prediction models to obtain a plurality of error messages; and
using the model verification module to determine that the candidate prediction models of one set of the candidate groups corresponding to one of the grouping numbers are optimal prediction models by comparing the error messages, wherein the prediction models associated with the groups are the optimal prediction models;
obtaining physiological data and hemodialysis treatment data of a first patient, wherein the first patient is one of the patients;
determining one of the groups to which the first patient belongs based on physiological characteristics of the first patient;
searching for a target prediction model from the prediction models based on the determined group; and
inputting the physiological data and the hemodialysis treatment data of the first patient to the target prediction model, and computing a recommended dehydration amount by the target prediction model.

2. The dehydration amount prediction method for hemodialysis according to claim 1, wherein the step of performing statistical analysis on the historical hemodialysis treatment data to obtain the physiological characteristic factors corresponding to the second patients respectively comprises:
obtaining a plurality of blood pressure values during hemodialysis from the historical hemodialysis treatment data of the patients; and
performing regression analysis on the blood pressure values to generate a plurality of blood pressure variation trend factors of the patients, wherein the blood pressure variation trend factors of the patients are a plurality of regression coefficients generated respectively based on the regression analysis.

3. The dehydration amount prediction method for hemodialysis according to claim 1, wherein the step of establishing the candidate prediction models respectively for all of the candidate groups by using the machine learning algorithm according to the historical physiological data and the historical hemodialysis treatment data of the patients comprises:
using a historical dehydration amount in the historical hemodialysis treatment data of the classified patients and the historical physiological data and the historical hemodialysis treatment data of the classified patients as a training data set of a supervised learning algorithm to train the candidate prediction models.

4. The dehydration amount prediction method for hemodialysis according to claim 1, further comprising:
displaying the recommended dehydration amount on a display interface, or setting an instrument parameter of an electronic medical device according to the recommended dehydration amount through the electronic device.

5. The dehydration amount prediction method for hemodialysis according to claim 4, further comprising:
calculating, through the electronic device, a dehydration amount per hour according to the recommended dehydration amount and preset dialysis time, and displaying the dehydration amount per hour on the display interface, or setting the instrument parameter of the electronic medical device according to the dehydration amount per hour.

6. The dehydration amount prediction method for hemodialysis according to claim 5, further comprising:
monitoring, through the electronic device, whether an actual dehydration amount of hemodialysis performed by the electronic medical device reaches the recommended dehydration amount or the dehydration amount per hour, and recording the actual dehydration amount.

7. The dehydration amount prediction method for hemodialysis according to claim 1, wherein the groups correspond to a plurality of group indexes respectively, and the method further comprises:
performing following through the electronic device:
in response to classifying the patients into the candidate groups, assigning each of the patients a corresponding one of the group indexes, wherein the step of determining one of the groups to which the first patient belongs comprises:
determining the one of the groups to which the first patient belongs according to one of the group indexes associated with the first patient.

8. The dehydration amount prediction method for hemodialysis according to claim 1, the method further comprising:
performing following through the electronic device:
after a preset period of time, reclassifying the patients into the candidate groups corresponding to the grouping numbers according to the historical physiological data and the historical hemodialysis treatment data of the patients, and retraining the candidate prediction models for the candidate groups by using the machine learning algorithm.

9. An electronic device, comprising:
a storage circuit, configured to store a plurality of modules; and
a processor, coupled to the storage circuit and configured to access the modules to:
constructe a plurality of prediction models associated with a plurality of groups respectively, including:
using a feature engineering module to obtain historical physiological data and historical hemodialysis treatment data of a plurality of patients;
using a grouping module to perform statistical analysis on the historical hemodialysis treatment data to obtain a plurality of physiological characteristic factors corresponding to the patients respectively;
using the grouping module to classify the patients into a plurality sets of candidate groups corresponding to a plurality of grouping numbers respectively based on the physiological characteristic factors;
using a model training module to establish a plurality of candidate prediction models respectively for all of the candidate groups by using a machine learning algorithm according to the historical physiological data and the historical hemodialysis treatment data of the patients;
using a model verification module to provide the historical physiological data and the historical hemodialysis treatment data of the patients to the candidate prediction models to obtain a plurality of error messages; and
using the model verification module to determine that the candidate prediction models of one set of the candidate groups corresponding to one of the grouping numbers are optimal prediction models by comparing the error messages, wherein he prediction models associated with the groups are the optimal prediction models;
obtain physiological data and hemodialysis treatment data of a first patient, wherein the first patient is one of the patients;
determine one of the groups to which the first patient belongs based on physiological characteristics of the first patient;
search for a target prediction model from the prediction models based on the determined group; and
input the physiological data and the hemodialysis treatment data of the first patient to the target prediction model, and compute a recommended dehydration amount by the target prediction model.

10. The electronic device according to claim 9, wherein the processor is further configured to:
obtain a plurality of blood pressure values during hemodialysis from the historical hemodialysis treatment data of the patients; and
perform regression analysis on the blood pressure values to generate a plurality of blood pressure variation trend factors of the patients, wherein the blood pressure variation trend factors of the patients are a plurality of regression coefficients respectively generated based on the regression analysis.

11. The electronic device according to claim 9, wherein the processor is further configured to:
use a historical dehydration amount in the historical hemodialysis treatment data of the classified patients and the historical physiological data and the historical hemodialysis treatment data of the classified patients as a training data set of a supervised learning algorithm to train the candidate prediction models.

12. The electronic device according to claim 9, wherein the processor is further configured to:
display the recommended dehydration amount on a display interface, or set an instrument parameter of an electronic medical device according to the recommended dehydration amount.

13. The electronic device according to claim 12, wherein the processor is further configured to:
calculate a dehydration amount per hour according to the recommended dehydration amount and preset dialysis time, and display the dehydration amount per hour on the display interface, or set the instrument parameter of the electronic medical device according to the dehydration amount per hour.

14. The electronic device according to claim 13, wherein the processor is further configured to:
monitor whether an actual dehydration amount of hemodialysis performed by the electronic medical device reaches the recommended dehydration amount or the dehydration amount per hour, and record the actual dehydration amount.

15. The electronic device according to claim 9, wherein the groups correspond to a plurality of group indexes respectively, and the processor is further configured to:
in response to classifying the patients into the candidate groups, assign each of the patients a corresponding one of the group indexes; and
determine the one of the groups to which the first patient belongs according to one of the group indexes associated with the first patient.

16. The electronic device according to claim 9, wherein the processor is further configured to:

after a preset period of time, reclassify the patients into the candidate groups corresponding to the grouping numbers according to the historical physiological data and the historical hemodialysis treatment data of the patients, and retrain the candidate prediction models for the candidate groups by using the machine learning algorithm.

* * * * *